United States Patent
Gross

(10) Patent No.: US 8,577,469 B2
(45) Date of Patent: Nov. 5, 2013

(54) IONTOPHORETIC AND ELECTROOSMOTIC DISC TREATMENT

(75) Inventor: Yossi Gross, Moshav Mazor (IL)

(73) Assignee: Rainbow Medical Ltd., Herzliya, IL (US)

(*) Notice: Subject to any disclaimer, the term of this patent is extended or adjusted under 35 U.S.C. 154(b) by 935 days.

(21) Appl. No.: 12/373,306

(22) PCT Filed: Jul. 10, 2007

(86) PCT No.: PCT/IL2007/000865
§ 371 (c)(1),
(2), (4) Date: May 27, 2009

(87) PCT Pub. No.: WO2008/007369
PCT Pub. Date: Jan. 17, 2008

(65) Prior Publication Data
US 2009/0312816 A1    Dec. 17, 2009

Related U.S. Application Data

(60) Provisional application No. 60/830,717, filed on Jul. 12, 2006.

(51) Int. Cl.
*A61N 1/00* (2006.01)
(52) U.S. Cl.
USPC .......................................................... 607/43
(58) Field of Classification Search
USPC ........................................... 607/43, 44
See application file for complete search history.

(56) References Cited

U.S. PATENT DOCUMENTS

| | | |
|---|---|---|
| 4,044,774 A | 8/1977 | Corbin et al. |
| 5,088,977 A | 2/1992 | Sibalis |
| 5,121,754 A | 6/1992 | Mullett |
| 5,433,739 A | 7/1995 | Sluijter et al. |
| 5,938,690 A | 8/1999 | Law et al. |
| 6,146,380 A | 11/2000 | Racz et al. |
| 6,161,047 A | 12/2000 | King et al. |
| 6,360,750 B1 | 3/2002 | Gerber et al. |
| 6,602,248 B1 * | 8/2003 | Sharps et al. .................. 606/32 |
| 6,620,155 B2 | 9/2003 | Underwood et al. |

(Continued)

FOREIGN PATENT DOCUMENTS

WO    2008007369 A2    1/2008

OTHER PUBLICATIONS

Vernengo J, "Injectable Bioadhesive Hydrogels for Nucleus Pulposus Replacement and Repair of the Damaged Intervertebral Disc: A Thesis", Drexel University (Jan. 2007).

(Continued)

*Primary Examiner* — Niketa Patel
*Assistant Examiner* — Minh Duc Pham
(74) *Attorney, Agent, or Firm* — Fish & Richardson P.C.

(57) ABSTRACT

Apparatus (10) is provided for treating an intervertebral disc (20) of a subject. The apparatus (10) includes a first electrode (30), configured to be inserted into a nucleus pulposus (40) of the disc (20), and a second electrode (32), configured to be placed outside of the nucleus pulposus (40), in a vicinity of the nucleus pulposus (40). A control unit (34) is configured to drive a current between the first and second electrodes (30, 32), and to configure the current to electroosmotically drive fluid between inside and outside the nucleus pulposus (40). Other embodiments are also described.

16 Claims, 1 Drawing Sheet

(56) References Cited

U.S. PATENT DOCUMENTS

| | | | |
|---|---|---|---|
| 6,997,941 B2 | 2/2006 | Sharkey et al. | |
| 7,223,227 B2 | 5/2007 | Pflueger | |
| 7,270,659 B2 | 9/2007 | Ricart et al. | |
| 7,398,121 B2 | 7/2008 | Matsumura et al. | |
| 7,831,306 B2 | 11/2010 | Finch et al. | |
| 2002/0151948 A1 | 10/2002 | King et al. | |
| 2003/0225331 A1 | 12/2003 | Diederich et al. | |
| 2004/0002746 A1* | 1/2004 | Ryan et al. | 607/99 |
| 2004/0019381 A1 | 1/2004 | Pflueger | |
| 2004/0049180 A1* | 3/2004 | Sharps et al. | 606/41 |
| 2004/0116977 A1 | 6/2004 | Finch et al. | |
| 2004/0210209 A1 | 10/2004 | Yeung et al. | |
| 2005/0010205 A1* | 1/2005 | Hovda et al. | 606/41 |
| 2005/0021104 A1* | 1/2005 | DiLorenzo | 607/45 |
| 2005/0277996 A1* | 12/2005 | Podhajsky | 607/46 |
| 2006/0030895 A1* | 2/2006 | Simon et al. | 607/43 |
| 2006/0224223 A1 | 10/2006 | Podhajsky et al. | |
| 2007/0000784 A1* | 1/2007 | Paul et al. | 204/600 |
| 2007/0073402 A1* | 3/2007 | Vresilovic et al. | 623/17.12 |
| 2008/0260542 A1* | 10/2008 | Nishikawa et al. | 417/48 |
| 2009/0126813 A1* | 5/2009 | Yanagisawa et al. | 137/831 |

OTHER PUBLICATIONS

Cheung KMC et al., "Intervertebral disc regeneration by use of autologous mesenchymal stem cells, an experimental model in rabbits", Abstract from the SRS 2004 Annual Meeting.

Freemont TJ et al., "Degeneration of Intervetebral disc: current understanding of cellular and molecular events, and implications for novel therapies", Expert Reviews in Molecular Biology, Mar. 29, 2001 (Cambridge University Press).

Urban JPG et al., "The necleus of the intervertebral disc from development to degeneration", American Zoologist 40(1):53-61 (2000).

An Office Action dated Apr. 11, 2013, which issued during the prosecution of U.S. Appl. No. 13/663,757.

* cited by examiner

IONTOPHORETIC AND ELECTROOSMOTIC DISC TREATMENT

CROSS-REFERENCES TO RELATED APPLICATIONS

The present application is the U.S. national phase of PCT Application No. PCT/IL07/000865 to Gross et al., filed Jul. 10, 2007, which claims the benefit of: U.S. Provisional Application 60/830,717, filed Jul. 12, 2006, entitled, "Iontophoretic and electroosmotic disc treatment" which is incorporated herein by reference.

FIELD OF THE INVENTION

The present invention relates generally to therapeutic electrical stimulation techniques, and specifically to apparatus and methods for therapeutic electrical stimulation of the spinal column.

BACKGROUND OF THE INVENTION

The intervertebral discs form cartilaginous joints between the end plates of vertebrae to provide shock absorption. The discs include two main regions: the nucleus pulposus, which is an inner, soft and highly hydrated structure, and the annulus fibrosus, which is a strong structure including lamellae (concentric sheets of collagen fibers), which surrounds the nucleus. The three major constituents of the discs are water, fibrillar collagens, and aggrecan. The proportion of these components varies across the disc, with the nucleus having a higher concentration of aggrecan and water and a lower collagen content than other regions of the disc. The loss of water content, particularly in the nucleus pulposus, is associated with disc degeneration, and with a decrease in disc height and abnormal loading of other spinal structures.

US Patent Application Publication 2005/0277996 to Podhajsky, which is incorporated herein by reference, describes a method for reducing intervertebral pressure, including providing an electrode, having proximal and distal ends, and a generator, which is operatively connected to the proximal end of the electrode, and is configured to supply radiofrequency current thereto. The method also includes inserting at least a portion of the distal end of the electrode into the nucleus pulposus of an intervertebral disc and activating the generator to heat the nucleus pulposus. The electrode may be inserted into the intervertebral disc through its first lateral side and/or its second lateral side, and may be substantially parallel to the major or minor axis of the nucleus pulposus.

U.S. Pat. No. 6,997,941 to Sharkey et al., which is incorporated herein by reference, describes a device that is positioned at a location in an intervertebral disc for diagnosis or treatment of the disc. Treatment may include, for example, applying energy or removing material, and may decrease intradisc pressure. Radiofrequency energy may be applied. A percutaneous method of repairing a fissure in the annulus pulposus comprises placing an energy source adjacent to the fissure and providing sufficient energy to the fissure to raise the temperature to at least about 45-70 degrees C., and for a sufficient time to cause the collagen to weld.

US Patent Application Publication 2003/0225331 to Diederich et al., which is incorporated herein by reference, describes an implantable ultrasound therapy system and method that provides directional, focused ultrasound to localized regions of tissue within body joints, such as spinal joints. An ultrasound emitter or transducer is delivered to a location within the body associated with the joint and heats the target region of tissue associated with the joint from the location. Such locations for ultrasound transducer placement may include, for example, in or around the intervertebral discs, or the bony structures such as vertebral bodies or posterior vertebral elements such as facet joints. Various modes of operation provide for selective, controlled heating at different temperature ranges to provide different intended results in the target tissue, which ranges are significantly affected by pre-stressed tissues such as in-vivo intervertebral discs.

US Patent Application Publication 2004/0116977 to Finch et al., which is incorporated herein by reference, describes a method for electrically stimulating an area in a spinal disc. The method comprises implanting a lead with one or more electrodes in a placement site in or adjacent to one or more discs at any spinal level from cervical through lumbar, connecting the lead to a signal generator, and generating electrical stimulation pulses using the generator to stimulate targeted portions of the disc. Additionally, a system for relieving pain associated with a spinal disc is described that comprises a lead with one or more electrodes, an introducer for introducing the lead to a placement site in or adjacent to the disc, a removable stylet for guiding the lead to the placement site in the disc, and a generator connected to the lead for generating electrical pulses to the lead for stimulating the disc.

US Patent Application Publication 2004/0019381 to Pflueger, which is incorporated herein by reference, describes spinal disc therapy systems including an element for implantation into an intervertebral disc annulus or intervertebral disc nucleus. The implant element includes a biochemically active agent that provides pain relief, inflammation relief, or other benefit. The implant element may include a mechanically active component that radiates wave energy, for example, in the form of electrical or magnetic energy.

US Patent Application Publication 2004/0049180 to Sharps et al., which is incorporated herein by reference, describes systems and methods for selectively applying electrical energy to a target location within a patient's body, particularly including tissue in the spine. High frequency (RF) electrical energy is applied to one or more electrode terminals in the presence of electrically conductive fluid or saline-rich tissue to contract collagen fibers within the tissue structures. In one aspect of the invention, a system and method is provided for contracting a portion of the nucleus pulposus of a vertebral disc by applying a high frequency voltage between an active electrode and a return electrode within the portion of the nucleus pulposus, where contraction of the portion of nucleus pulposus inhibits migration of the portion of nucleus pulposus through the fissure.

US Patent Application Publication 2004/0210209 to Yeung, which is incorporated herein by reference, describes methods for delivering and deploying conduits into an intervertebral disc to re-establish the exchange of nutrients and waste between the disc and bodily circulation, in order to stop or reverse disc degeneration and relieve pain. The intervertebral disc installed with semi-permeable conduits may be used as an immuno-isolated capsule to encapsulate donor cells capable of biosynthesizing therapeutic molecules. The semi-permeable conduits establish the exchange of nutrients and therapeutic molecules between disc and bodily circulation to treat a disease without using immuno-suppressive drugs.

The following references, all of which are incorporated herein by reference, may be of interest:

Vernengo J, "Injectable Bioadhesive Hydrogels for Nucleus Pulposus Replacement and Repair of the Damaged Intervertebral Disc: A Thesis," Drexel University (January 2007)

Cheung K M C et al., "Intervertebral disc regeneration by use of autologous mesenchymal stem cells, an experimental model in rabbits," Abstract from the SRS 2004 Annual Meeting Freemont T J et al., "Degeneration of intervertebral discs: current understanding of cellular and molecular events, and implications for novel therapies," Expert Reviews in Molecular Biology, Mar. 29, 2001 (Cambridge University Press)

Urban J P G et al., "The nucleus of the intervertebral disc from development to degeneration," American Zoologist 40(1): 53-61 (2000)

U.S. Pat. No. 6,161,047 to King
U.S. Pat. No. 4,044,774 to Corbin et al.
U.S. Pat. No. 6,146,380 to Racz et al.
U.S. Pat. No. 5,433,739 to Sluijter et al.
U.S. Pat. No. 5,121,754 to Mullett
U.S. Pat. No. 5,938,690 to Law et al.
U.S. Pat. No. 6,360,750 to Gerber et al.
US Patent Application Publication 2002/0151948 to King et al.

SUMMARY OF THE INVENTION

In some embodiments of the present invention, a system for treating an intervertebral disc comprises two electrodes, one of which is configured to be inserted into a nucleus pulposus of the disc, and the other to be placed outside of the disc. A control unit drives a current between the electrodes, and configures the current to electroosmotically drive fluid into the nucleus pulposus. Such an increase in fluid in the nucleus pulposus generally treats or prevents further degeneration of the disc caused at least in part by loss of fluid.

In some embodiments of the present invention, the control unit configures the current to electroosmotically drive fluid from the nucleus pulposus. Such a decrease in fluid in the nucleus pulposus generally reduces excess pressure in the disc caused at least in part by excessive fluid in the nucleus pulposus. Relief of such excess pressure may also reduce pain for some subjects.

In some embodiments of the present invention, at least one of the electrodes, such as the electrode placed outside of the disc, is coupled to a reservoir, and the control unit configures the current to iontophoretically drive a substance contained in the reservoir into the disc, such as into the nucleus pulposus and/or the annulus fibrosus. The substance comprises, for example, a drug (e.g., for pain relief), a hormone, or an agent for cell therapy. For some applications, the other one of the electrodes is also placed outside of the disc, rather than in the nucleus pulposus.

In some embodiments of the present invention, the techniques described herein are performed in combination with spinal cord stimulation techniques known in the art. For example, such spinal cord stimulation may be performed using stimulation systems marketed by Medtronic, Inc. (Minneapolis, Minn.).

There is therefore provided, in accordance with an embodiment of the invention, apparatus for treating an intervertebral disc of a subject, including:
a first electrode, configured to be inserted into a nucleus pulposus of the disc;
a second electrode, configured to be placed outside of the nucleus pulposus, in a vicinity of the nucleus pulposus; and
a control unit, configured to drive a current between the first and second electrodes, and to configure the current to electroosmotically drive fluid between inside and outside the nucleus pulposus.

For some applications, the second electrode is configured to be placed in the vicinity of an external surface of an annulus fibrosus of the disc. Alternatively, the second electrode is configured to be at least partially inserted into an annulus fibrosus of the disc.

For some applications, the apparatus includes an activity sensor, configured to detect a level of activity of the subject, and the control unit is configured to drive the current responsively to the detected level of activity. Alternatively or additionally, the apparatus includes an orientation sensor, configured to detect an orientation of the subject, and the control unit is configured to drive the current responsively to the detected orientation. For some applications, the control unit is configured to drive the current based on a circadian cycle of the subject.

For some applications, the first electrode includes a rigid support element having a non-conductive outer surface.

For some applications, the control unit is configured to configure the current to stimulate the formation of at least one type of new collagen fibers selected from the group consisting of: new collagen fibers in the nucleus pulposus, and new collagen in an annulus fibrosus of the disc.

For some applications, the first electrode is shaped so as to define a substance delivery channel. For some applications, the control unit is configured to apply heat to tissue in a vicinity of the disc. For some applications, the control unit is configured to generate oxygen by causing hydrolysis in at least one tissue selected from: the nucleus pulposus, and an annulus fibrosus of the disc.

In an embodiment, the control unit is configured to configure the current to electroosmotically drive the fluid into the nucleus pulposus. For some applications, the control unit is configured to configure the first electrode to have a negative charge, and the second electrode to have a positive charge.

In an embodiment, the control unit is configured to configure the current to electroosmotically drive the fluid from the nucleus pulposus. For some applications, the control unit is configured to configure the first electrode to have a positive charge, and the second electrode to have a negative charge.

In an embodiment, the apparatus includes a pressure sensor, configured to sense a pressure within the disc, and the control unit is configured to drive the current responsively to the sensed pressure. For some applications, the pressure sensor is integrated with the first electrode.

There is further provided, in accordance with an embodiment of the present invention, apparatus for delivering at least one substance to an intervertebral disc, including:
a reservoir, configured to contain the substance, and configured to be placed in a vicinity of an external surface of the disc;
a first electrode, coupled to the reservoir;
a second electrode; and
a control unit, configured to drive a current between the first and second electrodes, and to configure the current to drive the substance into the disc.

In an embodiment, the control unit is configured to configure the current to iontophoretically drive the substance into the disc.

In an embodiment, the control unit is configured to configure the current to cause electroporation.

For some applications, the control unit is configured to configure the current to drive the substance into a nucleus pulposus of the disc. Alternatively or additionally, the control unit is configured to configure the current to drive the substance into an annulus fibrosus of the disc.

For some applications, the first electrode is placed in the reservoir. Typically, the second electrode is configured to be placed in a location selected from the group consisting of: outside a nucleus pulposus of the disc in a vicinity of an external surface of the disc, in the nucleus pulposus, in an annulus fibrosus of the disc, and remotely from the disc.

For some applications, the substance is selected from the group consisting of: a drug, a hormone, an agent for cell therapy, and an agent for gene therapy, and the control unit is configured to configure the current to drive the selected substance into the disc. For some applications, the control unit is configured to set respective charges of the first and second electrodes responsively to a charge of the substance.

For some applications, the at least one substance includes first and second substances having opposite charges, the reservoir includes a first reservoir, which is configured to contain the first substance, and the apparatus includes a second reservoir, which is configured to contain the second substance.

For some applications, the control unit is configured to apply heat to tissue in a vicinity of the disc.

There is still further provided, in accordance with an embodiment of the present invention, apparatus for treating an intervertebral disc, including:

a first electrode, configured to be inserted into a nucleus pulposus of the disc; and a second electrode, electrically coupled to the first electrode, and configured to be placed outside of the nucleus pulposus, in a vicinity of the nucleus pulposus.

For some applications, the apparatus includes a conductor, which provides the electrical coupling of the first electrode to the second electrode.

In an embodiment, the apparatus includes a resistor, which is electrically coupled between the first and second electrodes. For some applications, the resistor has a variable resistance. For some applications, the apparatus includes a pressure sensor, which is configured to sense a pressure within the disc, and to set the resistance responsively to the sensed pressure. Alternatively or additionally, the apparatus includes a control unit, which is configured to set the resistance.

There is additionally provided, in accordance with an embodiment of the present invention, a method for treating an intervertebral disc of a subject, including:

driving a current between a first site within a nucleus pulposus of the disc and a second site outside of the nucleus pulposus; and configuring the current to electroosmotically drive fluid between inside and outside the nucleus pulposus.

For some applications, the method includes replacing the nucleus pulposus with an artificial substitute material before driving the current.

In an embodiment, configuring the current includes configuring the current to generate oxygen by causing hydrolysis in at least one tissue selected from: the nucleus pulposus, and an annulus fibrosus of the disc. For some applications, the method includes performing cell therapy supported at least in part by the generated oxygen.

There is yet additionally provided, in accordance with an embodiment of the present invention, a method for delivering at least one substance to an intervertebral disc, including:

placing the substance in a vicinity of an external surface of the disc; and iontophoretically driving the substance into the disc.

For some applications, the method includes replacing the nucleus pulposus with an artificial substitute material before driving the substance into the disc.

There is also provided, in accordance with an embodiment of the present invention, a method for treating an intervertebral disc, including:

identifying that the disc requires treatment; and treating the disc by:

inserting a first electrode into a nucleus pulposus of the disc, and placing a second electrode, which is electrically coupled to the first electrode, outside of the nucleus pulposus, in a vicinity of the nucleus pulposus.

For some applications, the method includes replacing the nucleus pulposus with an artificial substitute material before or during inserting of the first electrode.

The present invention will be more fully understood from the following detailed description of embodiments thereof, taken together with the drawings, in which:

DETAILED DESCRIPTION OF EMBODIMENTS

Figure 1:
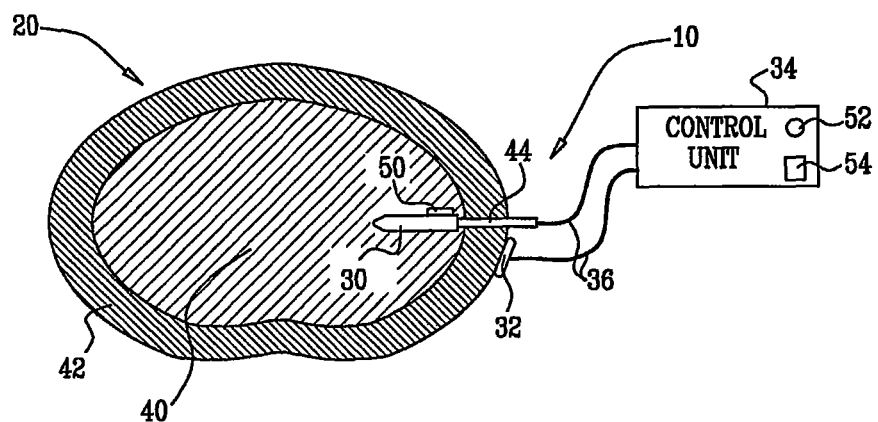
FIG. 1 is a schematic illustration of a system for treating an intervertebral disc, in accordance with an embodiment of the present invention.

FIG. 1 is a schematic illustration of a system 10 for treating an intervertebral disc 20, in accordance with an embodiment of the present invention. System 10 comprises first and second electrodes 30 and 32, and an implantable or external control unit 34, which is typically coupled to the electrodes by one or more electrode leads 36. First electrode 30 is configured to be inserted into a nucleus pulposus 40 of disc 20, and second electrode 32 is configured to be placed outside of the nucleus pulposus, in a vicinity of an external surface of an annulus fibrosus 42 of the disc, e.g., in physical contact with the external surface. Alternatively, second electrode 32 is configured to be at least partially inserted into annulus fibrosus 42 (configuration not shown). For some applications, the electrodes are placed during a conventional surgical procedure to repair the disc and/or the nucleus pulposus.

Control unit 34 drives a current between the first and second electrodes, and configures the current to electroosmotically drive fluid into nucleus pulposus 40. Typically, the control unit configures first electrode 30 to have a negative charge, and second electrode 32 to have a positive charge. Such an increase in fluid in the nucleus pulposus generally treats or prevents further degeneration of the disc caused at least in part by loss of fluid.

For some applications, the control unit configures the current with parameters including a voltage of up to about 1.8 volts, e.g., between about 0.1 volts and about 0.7 volts, or between about 0.7 volts and about 1.8 volts. Alternatively or additionally, the control unit configures the current with parameters including a current amplitude of less than about 3 mA, e.g., between about 0.1 and about 0.7 mA, or between about 0.7 and about 3 mA. For some applications, the control unit drives the current using a duty cycle. For example, the control unit may drive the current between about 1% and about 7% of the time, or between about 7% and about 50% of the time. In an embodiment, the current is driven based on the circadian cycle (e.g., while the patient is sleeping, or, alternatively, while the patient is awake). Alternatively or additionally, the current is driven based on feedback from a sensor, such as a pressure sensor that measures pressure within the disc, such as described hereinbelow.

For some applications, first electrode 30 comprises a rigid support element 44 having a non-conductive outer surface. The support element aids in the insertion of the electrode through annulus fibrosus 42 into nucleus pulposus 40, and in holding the electrode in place upon insertion.

In an embodiment of the present invention, control unit 34 configures the current to electroosmotically drive fluid from nucleus pulposus 40. In this embodiment, the control unit typically configures first electrode 30 to have a positive charge, and second electrode 32 to have a negative charge. Such a decrease in fluid in the nucleus pulposus generally reduces excess pressure in the disc caused at least in part by excessive fluid in the nucleus pulposus. Relief of such excess pressure may also reduce pain for some subjects.

In an embodiment of the present invention, first electrode 30 and second electrode 32 are electrically coupled to one another not via the control unit. For some applications, electrodes 30 and 32 are coupled to each other by a conductor (e.g., a wire), and providing such a short circuit between the inside and outside of nucleus pulposus 40 generally increases the positive charge of the nucleus pulposus, thereby driving fluid from the nucleus pulposus. For some applications, a resistor is electrically coupled between the electrodes. For some applications, the resistor has a variable resistance, which is adjusted automatically responsively to an intradisc pressure measured using pressure sensor 50, described hereinbelow. Alternatively or additionally, a control unit (either internal or external) is provided for adjusting the resistance.

In an embodiment of the present invention, system 10 further comprises a pressure sensor 50, which is configured to be placed in nucleus pulposus 40. For some applications, the sensor is coupled to or integrated with first electrode 30. Sensor 50 measures the intradisc pressure, and control unit 34 regulates application of the current responsively to the measured pressure, for example, to maintain a generally constant pressure within nucleus pulposus 40. Alternatively, the control unit varies a target pressure based on the time of day, an activity level (e.g., as measured by an accelerometer or heart rate monitor) or expected activity level of the subject, or other factors.

In an embodiment of the present invention, system 10 comprises a timer 52 and/or a sensor 54 that is configured to detect activity of the subject. For example, sensor 54 may comprise a motion detector, such as an accelerometer. For some applications, control unit 34 drives the current during only a portion of the time, such as only during the day, or only during the night, as determined using timer 52. Alternatively or additionally, control unit 34, responsively to a signal generated by activity sensor 54, drives the current only upon detecting a certain level of activity of the subject (such as exercise, or general motion indicative of wakefulness), or a certain level of inactivity (such as sleep). Further alternatively or additionally, the control unit drives the current responsively to an orientation of the subject, such as generally vertical or generally horizontal.

Alternatively, control unit 34 drives the current essentially continuously.

For some applications, control unit 34 configures the current to stimulate the formation of new collagen fibers in nucleus pulposus 40 (type II collagen) and/or in annulus fibrosus 42 (type I collagen). Such formation of new collagen fibers generally helps growth and repair of disc 20.

In an embodiment of the present invention, control unit 34 configures the current to cause hydrolysis in nucleus pulposus 40 and/or annulus fibrosus 42, thereby generating oxygen. Typically, the voltage applied by the control unit is greater than about 1.8 V, and the current is about 50-500 microamps or about 0.5-5 milliamps. Alternatively or additionally, other current parameters are utilized that are determined or known to be suitable for causing hydrolysis. Intervertebral discs, because they are not vascularized, depend on the end plates of the adjacent vertebrae to diffuse needed nutrients. For some applications, the oxygen generation provided by this embodiment is used to support cell therapy. As noted in the above-cited article by Cheung K M C, "Although there are many studies on stem cell therapy, the intervertebral disc may be a particularly challenging environment, as it is avascular and is subjected to large mechanical loads." Thus, the use of the techniques described herein for oxygen generation overcomes a significant hurdle for the clinically useful application of cell therapy in intervertebral discs.

In an embodiment of the present invention, first electrode 30 is shaped so as to define a substance delivery channel, through which a substance is delivered to nucleus pulposus 40.

Figure 2:
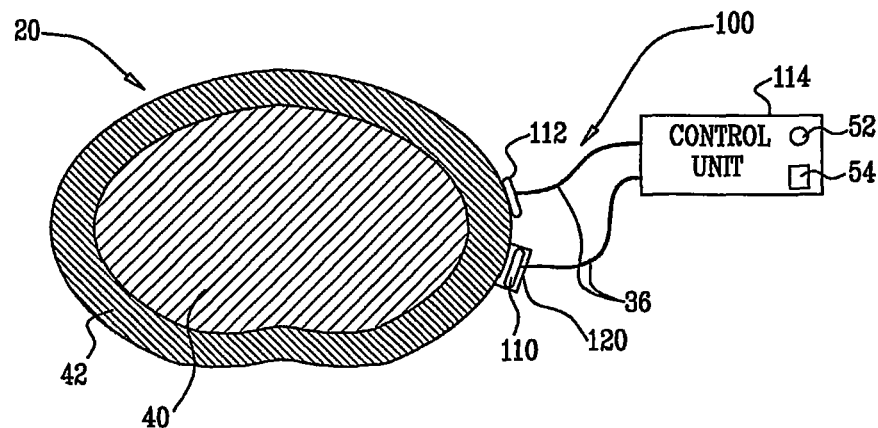
FIG. 2 is a schematic illustration of a system for iontophoretically delivering a substance to an intervertebral disc, in accordance with an embodiment of the present invention.

Reference is made to FIG. 2, which is a schematic illustration of a system 100 for iontophoretically delivering a substance to disc 20, in accordance with an embodiment of the present invention. System 100 comprises a reservoir 120 which contains the substance; a first electrode 110, which is coupled to (e.g., placed in) the reservoir; a second electrode 112; and an implantable or external control unit 114, which is typically coupled to the electrodes by one or more electrode leads 36. Reservoir 120 is configured to be placed in a vicinity of an external surface of disc 20, e.g., in physical contact with the external surface. For some applications, second electrode 112 is also configured to be placed in a vicinity of the external surface of the disc, e.g., in physical contact with the external surface, while for other applications the second electrode is configured to be inserted into nucleus pulposus 40 or into annulus fibrosus 42 (e.g., as shown in FIG. 1). Further alternatively, the second electrode is placed remotely from the disc; for example, the second electrode may be coupled to control unit 114, or a conductive portion of a can of the control unit may serve as the second electrode.

Control unit 114 configures the current to iontophoretically drive the substance contained in reservoir 120 into disc 20, such as into nucleus pulposus 40 and/or annulus fibrosus 42. The substance may comprise, for example, a drug (e.g., for pain relief), a hormone, or an agent for cell or gene therapy (e.g., stem cells or genes). The control unit configures the first and second electrodes to have appropriate charges based on the charge of the substance. For some applications, second electrode 112 is coupled to a second reservoir which contains a second substance having a charge opposite that of the substance contained in reservoir 120 (configuration not shown).

For some applications, control unit 114 drives the current using the parameters described hereinabove for system 10, with reference to FIG. 1. In an embodiment, the current is kept to a value less than about 2 mA, for applications in which this is sufficient to cause a desired rate of iontophoresis. For some applications, control unit 114 drives the current only a portion of the time, such as described hereinabove regarding system 10, with reference to FIG. 1. Alternatively or additionally, the control unit applies the current once every few days, such as for supporting cell or gene therapy.

In an embodiment of the present invention, control unit 114 configures the current to cause electroporation, such as for causing the passage of molecules that are not sufficiently charged to allow effective iontophoresis. The amplitude of the voltage applied to induce this electroporation is typically, but not necessarily, between about 50 and about 200 V, e.g., between about 100 and about 150 V. For some applications, such electroporation facilitates gene therapy.

For some applications, control unit 34 or 114 is configured to drive one or more of electrodes 30, 32, 110, or 112 (or another system component) to apply heat to tissue in a vicinity thereof, or to apply current configured for nerve stimulation, e.g., to block pain signals.

In an embodiment of the present invention, the techniques described herein are performed during or after replacement of the nucleus pulposus with an artificial substitute material, such as a hydrogel (a three-dimensional, hydrated polymer). For some applications, hydrogels and/or methods described in the above-mentioned thesis by Vernengo are used for this purpose.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating an intervertebral disc of a subject, comprising:
   driving a current between a first site within a nucleus pulposus of the disc and a second site outside of the nucleus pulposus; and
   configuring the current to electroosmotically drive fluid between inside and outside the nucleus pulposus.

2. The method according to claim 1, wherein the second site is in the vicinity of an external surface of an annulus fibrosus of the disc.

3. The method according to claim 1, wherein the second site is at least partially within an annulus fibrosus of the disc.

4. The method according to claim 1, wherein driving the current comprises detecting a level of activity of the subject, and driving the current responsively to the detected level of activity.

5. The method according to claim 1, wherein driving the current comprises detecting an orientation of the subject, and driving the current responsively to the detected orientation.

6. The method according to claim 1, wherein driving the current comprises driving the current based on a circadian cycle of the subject.

7. The method according to claim 1, wherein configuring the current comprises configuring the current to stimulate the formation of at least one type of new collagen fibers selected from the group consisting of: new collagen fibers in the nucleus pulposus, and new collagen in an annulus fibrosus of the disc.

8. The method according to claim 1, and comprising replacing the nucleus pulposus with an artificial substitute material before driving the current.

9. The method according to claim 1, wherein configuring the current comprises configuring the current to generate oxygen by causing hydrolysis in at least one tissue selected from: the nucleus pulposus, and an annulus fibrosus of the disc.

10. The method according to claim 1, wherein configuring the current comprises configuring the current to electroosmotically drive the fluid into the nucleus pulposus.

11. The method according to claim 10, wherein configuring the current comprises configuring the first site to have a negative charge, and the second site to have a positive charge.

12. The method according to claim 1, wherein configuring the current comprises configuring the current to electroosmotically drive the fluid from the nucleus pulposus.

13. The method according to claim 12, wherein configuring the current comprises configuring the first site to have a positive charge, and the second site to have a negative charge.

14. The method according to claim 1, wherein driving the current comprises sensing a pressure within the disc, and driving the current responsively to the sensed pressure.

15. A method for treating an intervertebral disc, comprising:
   identifying that the disc requires treatment; and
   treating the disc by:
      inserting a first electrode into a nucleus pulposus of the disc,
      placing a second electrode, which is electrically coupled to the first electrode, outside of the nucleus pulposus, in a vicinity of the nucleus pulposus, and,
      electroosmotically driving a fluid between the nucleus pulposus and the outside of the nucleus pulposus.

16. The method according to claim 15, and comprising replacing the nucleus pulposus with an artificial substitute material before or during inserting of the first electrode.

* * * * *